United States Patent [19]

Gilson et al.

[11] 4,077,444
[45] Mar. 7, 1978

[54] FRACTION COLLECTOR

[76] Inventors: Warren E. Gilson, 4801 Sheboygan Ave.; Robert E. Gilson, 4 Franklin Ave., both of Madison, Wis. 53705

[21] Appl. No.: 549,361

[22] Filed: Feb. 12, 1975

[51] Int. Cl.² .................. B65B 43/60; G01N 1/10
[52] U.S. Cl. .................................. 141/130; 23/259; 141/283
[58] Field of Search ................ 23/253, 259; 141/1, 141/130, 165, 168, 183, 184, 185, 186, 191, 250, 270, 283, 284, 312; 198/19, 131, 137, 138, 154, 158, 181, 339, 793, 797, 802

[56] References Cited

U.S. PATENT DOCUMENTS

| | | | |
|---|---|---|---|
| 2,894,542 | 7/1959 | Alm | 141/130 |
| 3,272,240 | 9/1966 | Roth | 141/283 X |
| 3,319,038 | 5/1967 | Meister et al. | 198/793 X |
| 3,570,555 | 3/1971 | Gilson | 141/130 X |
| 3,684,452 | 8/1972 | Bessman | 141/130 X |
| 3,854,507 | 12/1974 | Nishioka et al. | 141/130 |

Primary Examiner—Richard E. Aegerter
Assistant Examiner—Frederick R. Schmidt
Attorney, Agent, or Firm—Mason, Kolehmainen, Rathburn & Wyss

[57] ABSTRACT

A fraction collector wherein a head is aligned in sequence with individual containers of an array of containers so that fractions or samples may be deposited into the containers from a delivery tube supported by the head. A table surface slidingly supports a number of racks holding rows of containers. The racks are releasably attached to spaced points along a chain moved by a chain drive motor around a closed loop above the table surface. The head is supported above the path of the racks and is moved across the racks and along the rows by a head drive motor. A control circuit controls the chain and head drive motors to advance the chain in increments to position successive rows beneath the head, and moves the head in increments along the container rows to position the head above individual containers.

9 Claims, 4 Drawing Figures

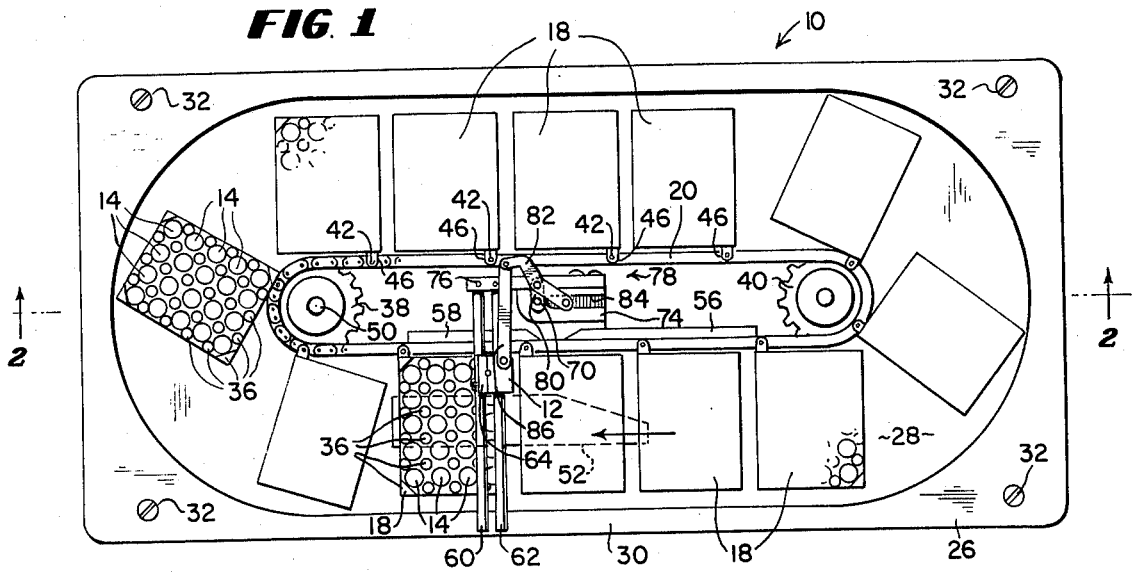

FRACTION COLLECTOR

The present invention relates to improvements in fraction collectors.

A fraction collector is a device for depositing individual samples, or fractions, from a supply of liquid, or sample column, into individual containers, typically test tubes. The size of each individual sample or fraction is determined by conventional measuring equipment such as a timer, a drop counter, or a level sensing device. The fraction collector includes a mechanism for sequentially aligning a head carrying a sample delivery conduit or tube over individual ones of an array of containers.

Many mechanisms have been developed for producing this sequential alignment of the head with individual containers. For example, in U.S. Pat. Nos. 3,221,781 and 3,272,240 there are described fraction collectors wherein test tube racks are moved over a surface to position individual tubes beneath a head. In U.S. Pat. No. 2,894,542 there is disclosed a fraction collector wherein a spiral array of tubes is rotated beneath a head and wherein the delivery tube is moved radially over individual tubes. In British Pat. No. 1,082,909 dated Dec. 14, 1965 there is disclosed a complex arrangement wherein racks holding rows of tubes are suspended by endless chains and move through a path between various work stations. Although not relating to fraction collectors, U.S. Pat. No. 1,065,787 illustrates an arrangement wherein racks carrying a number of containers are moved by a rotary turntable beneath a filling station.

It is of primary importance in the design of fraction collectors that the mechanism for aligning the head and individual containers be as simple and sturdy as possible while being reliably capable of precisely positioning the head and delivery tube in aligned positions over sequential containers. Fraction collectors known in the past including those disclosed in the above identified patents have been quite complex and therefore not only expensive but difficult to adjust and maintain. In particular, known fraction collector arrangements include tube and/or head drive mechanisms and indexing mechanisms which are extremely complicated and delicate.

It is an important object of the present invention to provide an improved fraction collector overcoming the disadvantages of known arrangements and characterized by simple, reliable and sturdy construction. Other important objects of the present invention are to provide a fraction collector including an improved and simple arrangement for advancing rows of tubes beneath a filling head; to provide a fraction collector including a simple and reliable indexing mechanism for locating rows of tubes beneath the head and for moving the head over individual tubes of the rows; and to provide a fraction collector wherein the use of delicate and complex mechanisms is avoided.

In brief, in accordance with the above and other objects of the present invention there is provided a fraction collector including a table surface for slidably supporting a number of racks each including structure for supporting containers in rows. A flexible endless member is mounted above the table surface for movement through a closed loop, and the endless member is advanced by means of a first drive motor. The racks are releasably attached to spaced points along the endless member so that they move through a closed loop-shaped path as the endless member is moved. A head having provision for supporting a sample column delivery tube is mounted for movement along a line intersecting the path of the racks, and a second drive motor is provided to move the head along the line. A control circuit coupled to the first and second drive motors advances the racks in increments for locating individual rows beneath the head, and moves the head in increments over individual containers of each row.

The invention together with the above and other objects and advantages will be best understood from consideration of the embodiment of the invention illustrated in the accompanying drawings, wherein:

FIG. 1 is a top plan view of a fraction collector constructed in accordance with the present invention;

FIG. 2 is a sectional view of portions of the fraction collector taken along the line 2—2 of FIG. 1;

Figure 3:
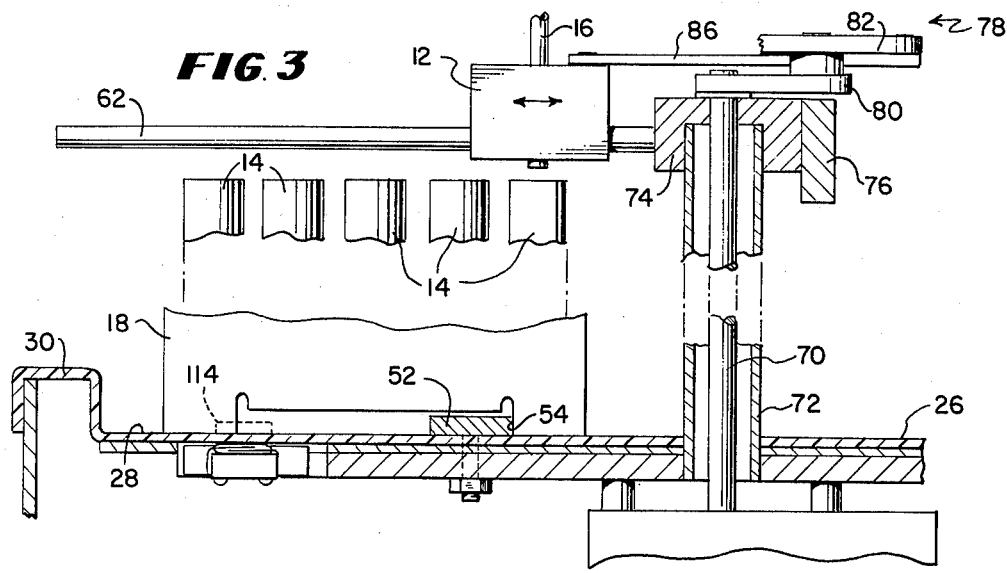
FIG. 3 is a fragmentary sectional view taken along the line 3—3 of FIG. 2.

Having reference now to the drawings, there is illustrated a fraction collector designated as a whole by the reference numeral 10 and constructed in accordance with the principles of the present invention. In general, the fraction collector 10 includes a head 12 positioned in sequence over containers or sample tubes 14 so that individual samples or fractions may be deposited into the tubes 14 from a liquid conduit or delivery tube 16. In accordance with the invention, the tubes 14 are disposed in racks 18 and the racks are moved around a closed, loop-shaped path by means of an endless member 20. Also in accordance with the invention there is provided a control circuit generally designated at 22 and illustrated in FIG. 4 for controlling the movement of the endless member 20 and the movement of the head 12 to provide the desired sequential relative positioning of the head over individual tubes 14.

Proceeding now to a more detailed description of the fraction collector 10, there is provided a housing or enclosure 24, the top of which is defined by a top member 26. Top member 26 is preferably a one-piece member formed for example of plastic or the like and serving to prevent spillage and the entry or foreign material into the interior of the housing 24. The member 26 is provided with a recessed central region 28 defining a slideway or track-like table surface along which the racks 18 are capable of sliding. A periperal flange portion 30 bounds the surface 28 and engages the upper side walls of the housing 24, and the top member 26 is held in place by suitable fasteners 32. If desired a drain (not shown) may be formed in the recessed surface 28 to carry away liquid deposited onto the top member 26 when a tube 14 is not beneath the head 12, for example after completion of a fraction collecting operation.

Each of the racks 18 may be similar to the others, and in the illustrated arrangement each rack 18 includes structure for supporting four rows of tubes 14, each row including five tubes. Each rack 18 may comprise an integral molded plastic unit including a base portion 34 and a number of upstanding supports or posts 36 defining interstices into which the tubes 14 may be placed. The racks 18 and top member 26 are preferably formed of material producing relatively low friction so that the racks 18 may readily be slid across the surface of the top member 26.

Although the endless member 20 may take many forms, in the illustrated arrangement it comprises a chain of conventional construction wherein individual links are pivotally related to one another. The chain 20 is mounted above the surface 28 of the top member 26 by a pair of sprockets 38 and 40 of which in the illustrated arrangement sprocket 38 is a drive sprocket and sprocket 40 is an idler sprocket. The chain 20 is consequently supported for movement in a closed loop having generally straight and parallel side segments extending between rounded segments at the sprockets 38 and 40.

Each rack is adapted releasably to be interconnected to the chain 20. More specifically, spaced links of the chain 20 are provided with drive pins 42. As can be seen in FIG. 2, each drive pin includes a nose portion extending upwardly of the chain 20 and a downwardly extending portion upon which is carried a slide shoe 44 slidably resting upon the surface 28 of the top member 26. As the chain 20 is advanced around its closed loop path, the pins 42 also move around the path with the shoes 44 maintaining each pin at the proper elevation. Each rack 18 includes a drive lug 46 formed integrally at one corner. The drive lugs 46 are apertured so that when the racks 18 are placed on the top member 26, the lug may be engaged with a drive pin 42 thereby releasably and drivingly interconnecting the racks 18 at spaced points along the chain 20.

A chain drive motor 48 is mounted within the housing 24 and includes a drive shaft 50 connected to the drive sprocket 38. The chain drive motor 48 is energized in a manner described below by the control circuit 22 in order to rotate the drive sprocket 38 and advance the chain 20 through predetermined increments of motion thereby to advance individual rows of containers 14 beneath the head 12.

In order precisely to position the racks 18 and thus the tubes 14 in the region of the head 12, a rack guide member 52 is carried by the surface 28 of the top member 26. As appears from a comparison of FIGS. 1 and 3, the guide member 52 engages an alignment wall portion 54 of the rack base 34.

Interfacing with the rack guide member 52 are a pair of chain back-up members or guides 56 and 58. These are engageable with the surface of the chain 20 opposite the racks 18, and since portions of the racks 18 and the chain 20 are sandwiched between the guide members 52, 56 and 58, the racks are properly positioned as they reach the region of the head 12.

Having reference now to the head 12, as appears in FIGS. 1-3 the head comprises a block-like body member having a pair of recesses for slidably mounting the head member on a pair of parallel slide rails 60 and 62 to the end that the head 12 is movable along a line intersecting and overlying the path of the racks 18. A clamp member 64 is carried by the head 12 for the purpose of clamping the discharge end of the fluid conduit or delivery tube 16 to the head 12.

In order to move the head 12 along its linear path overlying the rows of containers 14, a head drive motor 68 is mounted within the housing 24 and includes a drive shaft 70 extending upwardly above the top member 26 within a support column 72. A mounting block 74 is carried by the column 72 and in turn supports a bracket 76 upon which the slide rails 60 and 62 are mounted. Associated with the block 74 is a motion translation assembly 78 for converting rotary motion of the head drive motor shaft 70 to linear sliding motion of the head 12.

More specifically, the upper end of the drive shaft 70 is attached to one end of a rotating drive link 80. The outer end of link 80 is pivotally interconnected to the central portion of an alignment link 72. One extremity of the alignment link 82 is captured for linear sliding motion in a slideway or groove 84 in the mounting block 74, while the other end of the link 82 is pivotally connected to a connecting bar 86. The opposite end of the connecting bar 86 is pivotally connected to the head 12.

The motion translation assembly 78 functions to produce sliding motion of the head 12 in response to rotation of the motor drive shaft 70. As link 80 rotates around the end of drive shaft 70, the alignment link 82 is constrained to follow a cycle of movement wherein one of its ends reciprocates in the slideway 84 and the other end imparts alternate pushing and pulling motions to the connecting bar 86 and thus to the head 12.

Figure 4:
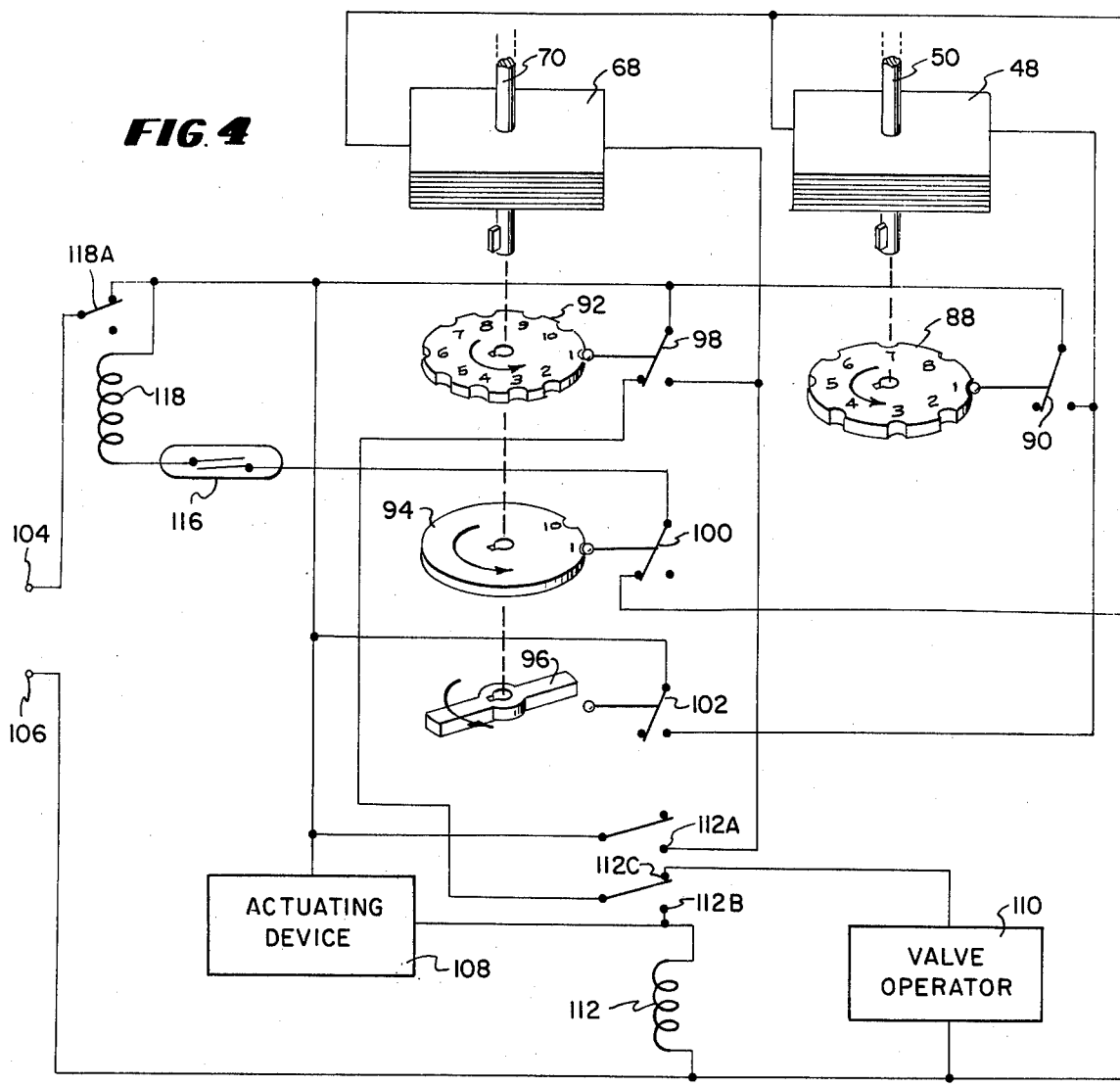
FIG. 4 is a schematic and diagrammatic illustration of portions of a control circuit for the fraction collector.

Position signals for controlling the operation of the control circuit 22 are provided in the illustrated arrangement by an assembly of cams and switches associated with the chain drive motor 48 and the head drive motor 68. More specifically, the drive shaft 50 of the chain drive motor 48 extends below the motor housing and supports a cam 88 controlling the operation of a switch 90 (FIGS. 2 and 4). In a similar manner, the drive shaft 70 of the head drive motor 68 is provided with three cams 92, 94 and 96 controlling switches 98, 100 and 102. It should be understood that other types of position sensing arrangements may be used if desired for providing signals in accordance with the positions of the rows of containers 14 and of the head 12.

Having reference now to FIG. 4, the control circuit 22 for the fraction collector 10 is illustrated in simplified schematic and diagrammatic form. The circuit 22 includes a pair of power supply terminals 104 and 106 adapted to be interconnected with a power source through suitable switching and protection circuits, control circuitry and the like. The switches 90, 98, 100 and 102 serve to control the energization of the motors 48 and 68 to produce sequential alignment of the head 12 over the containers 14. The switches are in turn controlled by the configurations of the cams 88, 92, 94 and 96.

More specifically, the cam 92 is configured to operate the switch 98 to its illustrated condition only when the shaft 70 of the head drive motor 68 is in a position wherein the head 12 directly overlies one of the tubes 14. In the illustrated arrangement, the containers or tubes 14 are disposed in rows of five tubes, and the cam 92 is provided with 10 recesses corresponding to two rows of the tubes. When the head 12 is not directly overlying one of the tubes 14, the switch 98 is operated to its alternate condition.

The cam 88 performs a somewhat similar function with regard to the chain drive motor 48. More specifically, the switch 90 is in its illustrated condition only when the shaft 50 of the chain drive motor 48 is in a position corresponding with the positioning of one of the rows of tubes beneath the head 12. The camm 88 is provided with eight switch operating indentations and consequently one revolution of the cam 88 corresponds with mmovement of the chain through a sufficient distance to move eight separate rows (or two racks) beneath the head 12. When the chain 20 is positioned such that the head 12 is between adjacent rows, the switch 90 is operated to its alternate position.

The cam 96 serves to operate the switch 102 from its illustrated to its alternate position twice during each full revolution of the shaft 70 associated with head drive motor 68. Cam 96 is aligned with cam 92 in such a way that switch 102 is operated when cam 92 is between the positions indicated as number ten and number one and the positions illustrated as number five and number six. Consequently, switch 102 closes when the head 12 has completed its motion over each entire row of tubes 14.

Cam 94 as discussed hereinafter controls an automatic shutoff operation of the fraction collector 10. This cam operates to close switch 100 only when the head 12 is at an end of its range of motion corresponding to the positions designated as number one and number ten on cams 94 and 92. The result of this arrangement is that the fraction collection cycle can be automatically stopped only when the head 12 and the fill tube 16 are in a predetermined region, as for example adjacent a drain in the top member 26.

Proceeding now to a description of the operation of the fraction collector 10, in accordance with known practice there is provided an actuating device shown in block form in FIG. 4 and designated by the reference numeral 108. The actuating device is functionally a switch and serves to complete a circuit in order to initiate movement of the head 12 from one tube to the sequentially next tube. For example, the actuating device may be controlled by a drop counter, a timer, or a level sensing device such that when a sample of predetermined size has been deposited into one tube 14, the actuating device is operated to initiate movement of the head 12 to the next adjacent tube. In its simplest form, the actuating device may comprise simply a manually operated switch closed in order to step the fraction collector 10 through one movement.

Also shown in block form in FIG. 4 is a valve operator designated by the reference numeral 110. In accordance with conventional practice, this valve operator may be associated with a valve controlling the flow of fluid through the delivery tube 16. The valve serves to discontinue flow through the tube during the period of time that the head 12 is moving between adjacent containers 14. The function of the valve operator 110 therefore is to prevent spillage from the tube 16 as it moves between positions.

As illustrated in FIG. 4, the fraction collector is in what may be termed the number one position also shown in FIGS. 1-3. In this position the head 12 and thus the delivery tube 16 is located directly over the first tube in the first row of tubes into which samples are to be deposited. In this position the valve operator 110 is energized by a circuit including the switch 98 so that the valve is opened and a fraction or a sample is permitted to flow into the tube.

At the end of the first fraction collection or sample deposit operation, the actuating device 108 is operated. Device 108 is connected in circuit between the power supply terminals 104 and 106 with the winding of a relay 112 including pairs of normally open contacts 112A and 112B and a pair of normally closed contacts 112C. Upon energization of relay 112, normally open contacts 112A close to complete a circuit for energization of the head drive motor 68. Consequently, shaft 70 commences rotation and the head 12 slides from its initial position over the first tube of the row to an adjacent position over the second tube of the row. Also in response to energization of relay 112, contacts 112C open to deenergize the valve operator 110, thus discontinuing flow of fluid through the delivery tube 16. Because actuating device 108 may comprise a momentary closing switch, contacts 112B are provided to form an alternate circuit for maintaining energization of relay 112 through contacts of switch 98 following momentary operation of the device 108.

As motor shaft 70 commences its rotation, switch 98 is operated from its illustrated to its alternate position as the cam 92 moves from the position designated as number one toward the position designated as number two. Although switch 98 opens the circuit for continued energization of the relay 112, it closes an alternate circuit for energization of the head drive motor 68 so that shaft 70 continues to rotate and head member 12 continues to move toward the second position.

When the head 12 reaches its second position directly overlying the second tube of the first row, switch 98 is reoperated to its illustrated condition and energization of the head drive motor 68 is discontinued. Since the contacts of relay 112 have returned to their illustrated condition at this time, a circuit is completed through switch 98 for energization of the valve operator 110. Consequently, fluid is once again permitted to flow through the delivery tube 16 to the second container 14. When the sample is deposited, actuating device 108 again operates to move the head 12 from the second to the third position as described above. Similar operations are repeated each time that the actuating device 108 is operated.

The fifth tube is the final tube in the row. As shaft 70 moves through its next increment of movement, cam 92 moves between the fifth and the sixth positions, and cam 96 comes into operation and closes the switch 102. This completes a circuit for energization of the chain drive motor 48 so that its shaft 50 rotates to advance the adjacent row of containers 14 beneath the head 12. As cam 88 rotates, switch 90 is operated to form an alternate path for maintaining energization of the chain drive motor 48. When the adjacent row of containers 14 is positioned beneath the head 12, cam 88 advances to its second position to reopen switch 90 thereby discontinuing energization of the chain drive motor 48.

Motors 68 and 48 continue to be periodically energized in response to periodic operations of the actuating device 108 so that in the manner described above the head 12 is moved in increments along the rows of containers 14 and so that after each row the racks 18 are advanced in increments to position adjacent rows beneath the head 12.

In order to provide for automatic shutoff of the fraction collector 10, a predetermined one of the racks 18 is provided with an embedded magnet 114 shown in broken lines in FIG. 3. A magnetically operated reed switch 116 is included in the control circuit 22 in series with the winding of a shutoff relay 118 having normally closed contacts 118A. When the magnet 114 overlies the switch 116, the switch 116 is operated to its closed position. Assuming that the head 12 is in its desired location corresponding with positions number one or number ten on the cam 94, a circuit is completed for energization of relay 118. Consequently, contacts 118A are operated to their open position thus deenergizing the control circuit 22.

While the invention has been described with reference to details of the illustrated embodiment, it should be understood that such details are not intended to limit the invention as defined in the following claims.

What is claimed and desired to be secured by Letters Patent of the United States is:

1. A fraction collector comprising in combination:
   housing means including a stationary generally horizontal surface,
   a flexible endless member,
   means mounting said endless member for movement around a closed loop above said surface;
   a plurality of racks slidably resting on said surface;
   each rack including structure for supporting at least one row of liquid containers;
   means releasably interconnecting said racks to spaced points along said endless member;
   first drive means for advancing said endless member in order to slide said racks around a closed path on said surface adjacent said loop;
   head means adapted to support a liquid conduit;
   support means for supporting said head means for movement along a line above said racks intersecting said path;
   second drive means for moving said head means along said line; and
   control means for operating said first and second drive means in increments for advancing said rows in sequence beneath said support means and for moving said head means in increments along said rows.

2. A fraction collector as claimed in claim 1, said endless member comprising a chain.

3. A fraction collector as claimed in claim 2, said releasably interconnecting means comprising drive pins at spaced points along said chain, and a single lug on each said rack pivotally engageable with one said drive pin.

4. A fraction collector as claimed in claim 3, each drive pin including a nose portion extending upwardly from said chain for engagement with said lug means, and a portion extending downwardly from said chain to a region adjacent said surface, and shoe means connected to said downwardly extending portion and slidable on said surface.

5. In a fraction collector of the type wherein liquid fractions are supplied from a conduit into containers, the combination comprising:
   a housing having a top wall defining a stationary generally horizontal surface;
   a plurality of racks slidable on said surface and including structure for supporting rows of said containers;
   an endless member;
   means supporting said endless member for movement in a closed loop adjacent and parallel to said surface;
   a first motor within said enclosure drivingly coupled to said endless member;
   means coupling said racks to spaced points along said endless member;
   slide means above said racks parallel with said rows;
   head means having structure for mounting said conduit;
   means for slidably mounting said head means on said slide means;
   a second motor within said enclosure drivingly coupled to said head means; and
   a control circuit for intermittently energizing said first and second motors for sliding said racks along said surface to position said rows in alignment with said slide means and for sliding said head means over individual containers of each row.

6. The combination of claim 5, said control circuit including cam means operated by said first and second motors, and switch means in circuit with said motors and operated by said cam means.

7. The combination of claim 5, said endless member comprising a chain positioned above said surface.

8. The combination of claim 5, said top wall comprising a one-piece molded member.

9. The combination of claim 8, said racks and said top wall being formed of plastic material providing low resistance to sliding of said racks along said top wall.

* * * * *